US00PP27734P2

(12) United States Plant Patent
Courtice

(10) Patent No.: US PP27,734 P2
(45) Date of Patent: Feb. 28, 2017

(54) ***HAKONECHLOA* PLANT NAMED 'HABSF1007'**

(50) Latin Name: *Hakonechloa macra*
Varietal Denomination: HABsf1007

(71) Applicant: Lyle G. Courtice, New Westminster, CA (US)

(72) Inventor: Lyle G. Courtice, New Westminster, CA (US)

( * ) Notice: Subject to any disclaimer, the term of this patent is extended or adjusted under 35 U.S.C. 154(b) by 0 days.

(21) Appl. No.: 14/757,191

(22) Filed: Dec. 2, 2015

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Penny J. Aguirre

(57) ABSTRACT

A new and unique cultivar of *Hakonechloa* named 'HABsf1007' that is characterized by its foliage that is deep burgundy-red to varying degrees that develops on emerging solid gold color foliage under higher light and chartruese to lime green with less intense burgundy-red in lower light, its foliage coloration that appears in the spring with emerging growth and lasts through summer into fall, foliage in the fall that turns to shades of green, red-purple and golden yellow/orange, its compact plant habit forming a low growing rounded mound with a slightly upright spikeness to the blades, its vigorous growth habit, and its cold hardiness at least to U.S.D.A Zone 5.

2 Drawing Sheets

Botanical classification: *Hakonechloa macra.*
Varietal designation: 'HABsf1007'.

BACKGROUND OF THE INVENTION

The present invention relates to a new and distinct cultivar of *Hakonechloa macra* and will be referred to hereafter by its cultivar name, 'HABsf1007'. 'HABsf1007' represents a new ornamental grass grown for landscape use.

The inventor discovered the new cultivar in spring of 2010 as a naturally occurring shoot mutation of *Hakonechloa macra* 'All Gold' (not patented) that was growing in a container in New Westminster, British Columbia, Canada.

Asexual reproduction of the new cultivar was first accomplished by shoot division in New Westminster, British Columbia, Canada in spring of 2012 by the Inventor. Asexual reproduction by shoot division and tissue culture has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'HABsf1007' as a unique cultivar of *Hakonechloa.*

1. 'HABsf1007' exhibits foliage that is deep burgundy-red to varying degrees that develops on emerging solid color foliage under higher light and chartruese to lime green with less intense burgundy-red in lower light.
2. 'HABsf1007' exhibits foliage coloration that appears in the spring with emerging growth and lasts through summer into fall.

3. 'HABsf1007' exhibits foliage in the fall that turns to shades of green, red-purple and golden yellow/orange.
4. 'HABsf1007' exhibits a compact plant habit forming a low growing rounded mound with a slightly upright spikeness to the blades.
5. 'HABsf1007' exhibits a vigorous growth habit.
6. 'HABsf1007' exhibits'cold hardiness at least to U.S.D.A. Zone 5.

The female parent *Hakonechloa* 'All Gold' (not patented) of 'HABsf1007', differs from 'HABsf1007' in having leaves that are solid gold in color and stay solid gold in color all year with no burgundy-red coloration. 'HABsf1007' can also be compared to cultivars of *Hakonechloa* 'Beni-Kaze' (not patented) and *Hakonechloa* 'Nicolas' (U.S. Plant Pat. No. 19,898) 'Beni-Kaze' is similar to 'HABsf1007' in having foliage that turns reddish-purple in coloring. 'Beni-Kaze' differs from 'HABsf1007' in having foliage that is solid green in color and only shows reddish-purple coloration in late summer and fall, in being less cold hardy, in having a high rate of reversion, and in having less vigor. 'Nicolas' is similar to 'HABsf1007' in having foliage that exhibits some red tones. 'Nicolas' differs from 'HABsf1007' in having foliage that is solid green in color and only exhibits orange and red coloration in fall with the onset of cool weather and in having less vigor.

BRIEF DESCRIPTION OF THE DRAWINGS

The accompanying colored photographs illustrate the overall appearance and distinct characteristics of the new cultivar of *Hakonechloa* as grown outdoors in New Westminster, British Columbia, Canada.

The photograph in FIG. 1 was taken of a 6 year-old plant as grown in a 2-gallon container. The photograph in FIG. 1 provides a side view of a plant of 'HABsf1007' in bloom.

Figure 1:
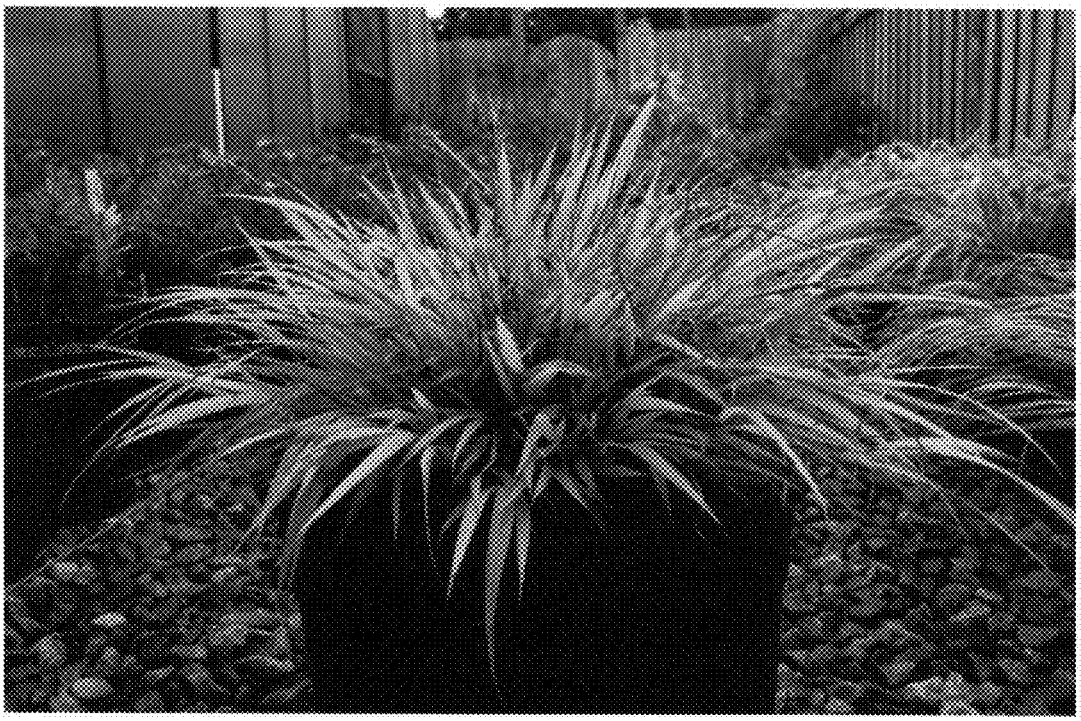
Figure 2:
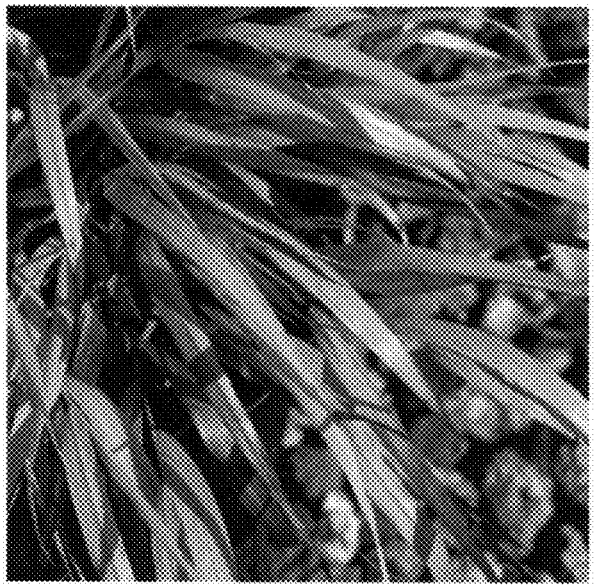

The photograph in FIG. 2 was taken of a 2 year-old plant as grown in a 1-gallon container and provides a close-up view of the spring and summer foliage of 'HABsfF1007'.

Figure 3:
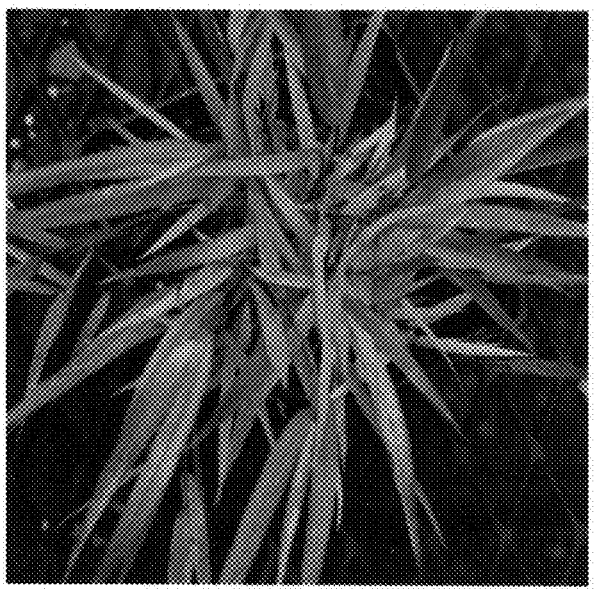

The photograph in FIG. 3 was taken of three to four month-old plant grown in a 4-inch pot from a 72-cell plug (tissue culture). The photograph in FIG. 3 provides a view of the fall foliage of 'HABsf1007'.

The colors in the photographs may differ slightly from the color values cited in the detailed botanical description, which accurately describe the colors of the new *Hakonechloa*.

BOTANICAL DESCRIPTION OF THE PLANT

The following is a detailed description of 5 month-old plants of 'HABsf1007' as grown outdoors in 4-inch containers in Aldergrove, British Columbia, Canada. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming habit*.—Late summer into early fall in British Columbia, Canada.

*Plant type*.—Herbaceous grass.

*Plant habit*.—Compact plant habit forming a low growing rounded mound with a slightly upright spikeness to the blades.

*Height and spread*.—An average of 30 to 45 cm in height and 45 to 60 cm in spread as a 3 to 5 year-old plant in the landscape.

*Cold hardiness*.—At least to U.S.D.A. Zone 5.

*Diseases and pests*.—No susceptibility or resistance to diseases or pests has been observed.

*Root description*.—Fibrous, 164D in color.

*Propagation*.—Tissue culture and stem division.

*Vigor*.—Slow to moderate with a compact habit.

*Root development*.—Will fully develop in a one-gallon container in 6 to 8 months from a 72-cell plug (from tissue culture).

Culm (stem) description:

*General*.—Round, sheathed.

*Culm color*.—144B (covered by leaf sheeth 144B and suffused with a blend of 165A and 166B).

*Culm size*.—Average of 12.5 cm in length and 1 mm in width.

*Stem surface*.—Glabrous and satiny.

*Stem number*.—About 40 in a 4-inch container.

*Internode length*.—Average of 1.3 cm.

*Branching*.—Basal branches only, no lateral branches.

Foliage description:

*Leaf shape*.—Lanceolate.

*Leaf division*.—Simple.

*Leaf base*.—Cuneate and decurrent at stem.

*Leaf apex*.—Acuminate-like but tapering to a very fine point.

*Leaf aspect*.—Held upward at about a 30° angle to vertical.

*Leaf venation*.—Parallel, matching leaf color.

*Leaf margins*.—Entire.

*Leaf attachment*.—Sheathed.

*Leaf size*.—Leaf blade; an average of 8 mm in width and 9 cm in length, sheathed portion; an average of 1.3 cm in length and 1 mm in width.

*Leaf number*.—Average of 7 per culm 12 cm in length.

*Leaf arrangement*.—Alternate.

*Ligule*.—183C in color, with a band of tufted hairs N155A in color, 1.5 mm in width and 1 mm in height.

*Leaf surface*.—Glabrous and dull on upper and lower surface.

*Leaf color*.—Emerging leaves, upper surface and lower surface; 144B, mature leaves (spring through early fall) upper and lower surface; a blend of N144A and N144B and variably heavily suffused with a blend of 183A and 166A, fall color upper and lower surfaces; a blend of primarily 145D, 138D, N82C, and 163C.

Inflorescence description:

*General description*.—Terminal airy panicle of single spikelets.

*Lastingness of inflorescence*.—Each panicle blooms for about 3 weeks, persistent.

*Fragrance*.—None.

*Panicle size*.—Average of 6 cm in length and up to 4 cm in width.

*Panicle number*.—One per culm.

*Rachis*.—An average of 4.5 cm in length (continuous with culm), 0.5 mm in diameter, 143D in color, with rachilla emerging to about a 45° angle to culm.

*Spikelet bud*.—About 6 mm in length and 1 mm in width, narrow lanceolate in shape, 145C to 145D in color.

*Spikelet description*.—Single floret enclosed by one glume and one lemma, glume; lanceolate in shape with a glabrous surface, entire margin, acute apex, 6 mm in length, 1 mm in width and 145D and suffused with 185B in color, lemma; lanceolate in shape with a glabrous surface, entire margin, acute apex, 6.5 mm in length, 1 mm in width and 145D and suffused with 185B in color.

*Spikelet number*.—Average of 60 per panicle.

*Spikelet size*.—About 7 in length and 4 mm in width.

Reproductive organs:

*Stamens*.—2, anthers are dorsifixed, x-shaped, about 2 mm in length and 187A in color, pollen was not observed.

*Pistils*.—2, about 1.5 mm in length, stigma is fimbriate in shape, about 0.5 mm in length, and N77C in color, style; transparent in color, about 0.5 mm in length, ovary is 145A in color.

*Seed*.—Seed development has not been observed.

It is claimed:

1. A new and distinct cultivar of *Hakonechloa* plant named 'HABsf1007' as herein illustrated and described.

* * * * *